(12) United States Patent
Gündel et al.

(10) Patent No.: US 8,380,287 B2
(45) Date of Patent: Feb. 19, 2013

(54) METHOD AND VISUALIZATION MODULE FOR VISUALIZING BUMPS OF THE INNER SURFACE OF A HOLLOW ORGAN, IMAGE PROCESSING DEVICE AND TOMOGRAPHIC SYSTEM

(75) Inventors: Lutz Gündel, Erlangen (DE); Michael Scheuering, Nürnberg (DE)

(73) Assignee: Siemens Aktiengesellschaft, Munich (DE)

(*) Notice: Subject to any disclaimer, the term of this patent is extended or adjusted under 35 U.S.C. 154(b) by 510 days.

(21) Appl. No.: 12/457,633

(22) Filed: Jun. 17, 2009

(65) Prior Publication Data
US 2009/0318800 A1 Dec. 24, 2009

(30) Foreign Application Priority Data
Jun. 18, 2008 (DE) .......................... 10 2008 028 945

(51) Int. Cl.
*A61B 5/05* (2006.01)
*G06K 9/00* (2006.01)
*G06T 15/40* (2011.01)

(52) U.S. Cl. ......... 600/425; 600/407; 382/131; 345/421
(58) Field of Classification Search .......... 345/419–424; 382/128–131; 600/407
See application file for complete search history.

(56) References Cited

U.S. PATENT DOCUMENTS
2006/0221074 A1 10/2006 Matsumoto
2008/0055308 A1 3/2008 Dekel

OTHER PUBLICATIONS

German Office Action dated Jan. 28, 2009.
Anna Vilanova i Bartroli et al.. "Visualization Techniques for Virtual Endoscopy", Dissertation, Technische Universität Wien, 2001; Others.
Markus S. Juchems et al., "CT colonography: comparison of a colon dissection display versus 3D endoluminal view for the detection of polyps", Eur. Radiol. (2006) 16: pp. 68-72, DOI 10.1007/s00330-005-2805-y; Others.

*Primary Examiner* — Michael Rozanski
(74) *Attorney, Agent, or Firm* — Harness, Dickey & Pierce, P.L.C.

(57) ABSTRACT

A method is disclosed for visualizing bumps of the inner surface of a hollow organ. In at least one embodiment, the method includes acquiring recorded image data of the hollow organ using an imaging system; drawing a cutting edge in the image data along the surface of the hollow organ in the longitudinal direction; preparing the image data to display the surface of the hollow organ along a plane on which the surface is plotted in an opened-up fashion; and changing a viewing angle and/or an illumination angle during a display of the hollow organ, a rotation of the plane along an axis running parallel to the cutting edge and/or along an axis running transversely to the cutting edge being carried out to change the viewing angle. A visualization module, an image processing device with such a visualization module and a tomographic system with such an image processing system.

23 Claims, 3 Drawing Sheets

METHOD AND VISUALIZATION MODULE FOR VISUALIZING BUMPS OF THE INNER SURFACE OF A HOLLOW ORGAN, IMAGE PROCESSING DEVICE AND TOMOGRAPHIC SYSTEM

PRIORITY STATEMENT

The present application hereby claims priority under 35 U.S.C. §119 on German patent application number DE 10 2008 028 945.0 filed Jun. 18, 2008, the entire contents of which are hereby incorporated herein by reference.

FIELD

At least one embodiment of the present invention generally relates to a method for visualizing bumps of the inner surface of a hollow organ. Furthermore, at least one embodiment generally relates to a visualization module for visualizing bumps, an image processing device with such a visualization module and/or a tomographic system with such an image processing system.

BACKGROUND

The visualization of image data of the inner surface of hollow organs, for example a blood vessel or an intestine, or sections thereof, often is used to detect bumps of these inner surfaces. These bumps can be the result of, for example, growths such as polyps or lesions. A person examining the inner surface of a hollow organ for bumps therefore wants to ensure that no bump, from which dangerous symptoms may be inferred, remains unnoticed.

For the purposes of visualization, it is possible to produce so-called multi-planar reconstructions, i.e. slice images, in a so-called two-dimensional workflow of volume data records of a volume data record region comprising a hollow organ. The slices are usually orthogonal with respect to the patient axes or to the axes of a hollow organ or a body comprising the hollow organ. The multi-planar reconstructions are examined for suspicious structures and possibly marked thereafter. Subsequently, the marked location of the image data record can be examined and processed further using three-dimensional displays, e.g. using the volume rendering technique or a surface shaded display.

As an alternative to the two-dimensional workflow, the reverse path can be undertaken in the three-dimensional workflow: the image data of a hollow organ filled with a contrast agent, for example air or carbon dioxide, are segmented. Subsequently, a so-called virtual flight is carried out through the hollow organ. In the process, the hollow organ surface is displayed by means of a surface shaded display. A suspicious location is marked by a user, and the workstation immediately displays identical positions in one or more multi-planar reconstructions of the volume data record. The suspicious location is made visible with the aid of this display.

Using the two-dimensional workflow, different data records, for example those which were generated in the prone and dorsal positions of a patient, can be examined very rapidly. By contrast, the advantage of the three-dimensional workflow is that significantly more bumps can be found. However, due to the presence of a multiplicity of usual bumps in hollow organs, e.g. the intestinal folds in the case of a scan of the intestine, this is also connected to increased time expenditure.

In order to reduce this disadvantage in terms of speed, so-called virtual dissection can be used. To put it simply, the hollow organ is in this case considered to be a tube which is cut open in the longitudinal direction, spread open and displayed in the plane of a screen. The visualization of bumps is found to be particularly difficult in the case of virtual dissection because it in turn is a purely two-dimensional form of display.

US 2006/0221074 A1, the entire contents of which are hereby incorporated herein by reference, illustrates such a virtual dissection. Moreover, this publication shows how the surface of a hollow organ can be scanned virtually using a so-called ray casting method. Furthermore, US 2008/0055308 A1 describes that such a ray casting is particularly effective in recognizing lesions and objects hidden behind bumps when the location of the ray caster, that is to say a sending unit (referred to as a camera in this document), is displaced along the profile of the hollow organ. This can be performed both in a three-dimensional image and in the display of the virtual dissection.

SUMMARY

At least one embodiment of the present invention provides a possibility by which bumps—specifically malignant bumps—which are present on the inner surface of a hollow organ can be visualized more easily and more effectively.

According to at least one embodiment of the invention, a method is disclosed for visualizing bumps of the inner surface of a hollow organ, comprising:

acquiring recorded image data of the hollow organ using an imaging system, drawing a cutting edge in the image data along the surface of the hollow organ in the longitudinal direction, preparing the image data to display the surface of the hollow organ along a plane on which the surface is plotted in an opened-up fashion, changing a viewing angle and/or an illumination angle during a display of the hollow organ, a rotation of the plane along an axis running parallel to the cutting edge and/or along an axis running transversely to the cutting edge being carried out.

Thus, in principle, at least one embodiment of the invention uses virtual dissection which is supplemented by the steps according to at least one embodiment of the invention. In the process, an overlap region which runs along the cutting edge can also be displayed twice so that bumps in this overlap region can be shown in their entirety. The cutting edge runs along the longitudinal direction of the hollow organ, that is to say in its progression direction of the hollow organ or in the through-flow direction of fillings which pass through the hollow organ, for example in the through-flow direction of blood in the case of arteries or digested food or stool in the case of an intestine, or in the opposite direction. In order to be able to draw such a cutting edge, it may additionally be necessary to virtually stretch the hollow organ so that it obtains a substantially straight-lined profile. For example, this is necessary in the virtual dissection of a large intestine because the latter has a multiplicity of loops.

Following the virtual dissection, a visualization or a simplification of the visualization is now performed using three method steps, which can be applied on their own but can also be combined with each other where necessary. In this case, the display is preferably effected on a graphical user interface such as a computer screen. The display plane thereof is, at the same time, usually the initial display plane of the virtual dissection. In particular in the case of a method in accordance with the third variant, it is also possible for a different type of display, for example an image print-out, to be selected.

In the two variants according to at least one embodiment of the invention, the display of the surface of the hollow organ is varied dynamically. This makes it possible for a user to visually detect bumps more easily. In the case of changing the viewing angle, this is effected in a manner similar to a holographic 3D display when moving a hologram: to the observer, the image moves during the virtual rotation of the plane around an axis such that said observer automatically detects hidden structures therein, for example by a movement of shadows or by a region lying behind a bump in the viewing direction being covered slowly. By contrast, in a purely static display of a plane many of such structures initially remain undetected.

The dynamization of the illumination situation works in a similar fashion by varying an illumination angle: here bumps can basically be detected by the movement of the shadows caused thereby. An illumination angle in an image display is created by the use of a virtual illumination by way of a virtual light source. The latter is always used when a two-dimensional display should be prepared quasi three-dimensionally for a user. The illumination makes it possible for structures to be detected more easily, and shadows of these structures result. The angle of illumination of such a virtual light source on the one hand, and, on the other hand, the lamp aperture angle, i.e. the angle covered by the light fan of the light source, can be defined in this case as the illumination angle. By varying one of the two or both illumination angles, shadows caused by bumps move on in the display and so a user can detect the bumps more easily.

Two variants of at least one embodiment of the invention which can be used alternatively, or supplement each other, provide for rotations of the plane along axes in order to change the viewing angle. In the process, in accordance with a first variant, a rotation of the plane along an axis running parallel to the cutting edge is selected; in accordance with a second variant, it is a rotation of the planes along an axis running transversely, preferably orthogonal, to the cutting edge.

The rotation along an axis running parallel to the cutting edge provides an advantage inasmuch as it forms a more direct reference for the observer: since the display of hollow organs in the virtual dissection is usually plotted in the longitudinal direction, row by row and from left to right, rotation is effected parallel to the direction of the display of the hollow organ and this can be comprehended more easily by a user. Depending on the area of application and the method of displaying the virtual dissection, it is however also possible for an axis which is transverse to the cutting edge to be selected; mainly in addition to the rotation along the first-mentioned axis, but also applied on its own if required, for example for special effects. A combination of the two types of rotation can be effected here both simultaneously and successively. The axis preferably runs through the center of an image display so that the user is not confused optically.

In addition, it is possible for a graphical clarification of the height conditions of the surface in relation to the plane to be effected. By way of example, this can be effected, even statically, by height contour displays analog to a geographic map and/or by different coloring or brightness. Such a height contour display of a virtual dissection is presented in Vilanova i Bartolí, Anna: Visualization Techniques for Virtual Endoscopy. Diss. Technische Universität Wien (Technical University Vienna) 2001 (Chapter 8.5), the entire contents of which are hereby incorporated herein by reference. An intuitively graspable picture of the height is provided for the observer in this fashion, with bumps becoming recognizable even in their basic structure—for example, whether a bump is a channel-like depression or a hemispherical bulge.

Using the visualization methods described here, a user can quickly and very reliably recognize bumps and, additionally, can in principle differentiate between different types of bumps. By way of example, if the inner surface of a large intestine is examined, it typically has folds across the progression direction. These folds are usually only of little interest, unlike approximately hemispherical bulges from which, for example, lesions or polyps can be deduced.

Moreover, at least one embodiment of the invention is directed to a visualization module for visualizing bumps of the inner surface of a hollow organ, comprising:
  an input interface for image data of the hollow organ from an imaging system,
  a cutting edge definition unit for drawing a cutting edge in the image data along the surface of the hollow organ in the longitudinal direction,
  a preparation unit for preparing the image data to display the surface of the hollow organ along a plane E on which the surface is plotted in an opened-up fashion,
  a visualization-support unit which generates visualization data from the image data and is designed such that during operation it changes a viewing angle and/or an illumination angle while the hollow organ is displayed, a rotation of the plane along an axis running parallel to the cutting edge and/or along an axis running transversely to the cutting edge being carried out to change the viewing angle,
  an output interface for the visualization data.

A display in the form of a virtual dissection is generated from the image data in the cutting edge definition unit and the preparation unit. The visualization-support unit is used to visualize bumps in said virtual dissection by using the above-mentioned measures. In order to change the viewing angle or the virtual illumination angle or the graphical display of the height conditions, a display logic is stored either in the visualization-support unit or in a memory connected thereto. In the case of a visualization-support unit, in which the viewing or the illumination angle is varied, said display logic is designed analogously to graphics display systems, as are used, for example, in CAD (computer aided drawing) systems.

Objects or planes are also rotated virtually here and a virtual illumination situation is varied. The rotation of the display plane, or the change in the illumination angle, can be effected automatically both in such programs and in the visualization module according to at least one embodiment of the invention and/or it can be controlled by a user, for which purpose provision can be made for a corresponding user interface in the visualization module.

In contrast, in the case of a visualization-support unit in which the height conditions are displayed graphically, the display logic is based on systems from cartography.

The interfaces do not necessarily have to be designed as hardware components, but can also be implemented as software modules, for example if all of the image data or parts thereof can be taken from another component already implemented on the same piece of equipment, such as, for example, an image reconstruction apparatus for a tomographic system or the like, or if they only have to be transferred in software terms to another component. Likewise, the interfaces can also include hardware and software components, such as, for example, a standard hardware interface which is specifically configured for the concrete application by software. Furthermore, the two interfaces can also be combined in a combined interface, for example an input/output interface.

Overall, a large proportion of the components for implementing the visualization module in the manner according to at least one embodiment of the invention, in particular the cutting edge definition unit, the preparation unit and the visualization-support unit, can, in total or in part, be implemented on a processor in the form of software modules.

It is for this reason that at least one embodiment of the invention also relates to a computer program product, which can be loaded directly into a processor of a programmable image processing system, with program code segments, in order to execute all steps of a method according to at least one embodiment of the invention when the program product is executed on the image processing system.

Moreover, at least one embodiment of the invention relates to an image processing device with a visualization module according to at least one embodiment of the invention and a tomographic system, in particular a computed tomography or magnetic resonance imaging scanner, with such an image processing system.

Additional particularly advantageous refinements and developments of at least one embodiment of the invention emerge from the dependent claims and the following description. Here, the visualization module can also be developed according to the dependent claims of the analogous method.

An example embodiment of the invention provides for a change of position of a virtual light source. This can be a change in location of the light source within a plane extending parallel to the display plane and/or a movement of the light source out of said plane, for example in order to, in end effect, illuminate the display plane directly from above. As a result of changing the position, the illumination angle is automatically changed while the hollow organ is displayed. This results in a movement of the shadow during the change in position. Therefore, a user, very intuitively and also with limited previous knowledge regarding the topology of hollow organs, can recognize differences in the bumps and correspondingly differentiate between conspicuous and inconspicuous bumps. An approximately hemispherical lesion, for example, always throws a shadow with practically the same shape when a position of a virtual light source is changed, said shadow only disappearing when the virtual light source lies exactly perpendicularly above the lesion. By contrast, the shadow of less regular bumps, for example the folds of the large intestine, can only be recognized in some illumination perspectives—and is only suggested in others. Moving the virtual light source reveals this change of the shadow.

In accordance with an advantageous development of this embodiment, a plurality of virtual light sources is used. This additionally results in better assessment possibilities regarding the type and quality of the bumps. In particular, the switching on and/or switching off of additional virtual light sources can in this case cause a particular effect. A user firstly detects a conspicuous bump from its moving shadow due to a first virtual light source. Switching on the second or a further virtual light source can provide more information about the type of bump.

Within the scope of at least one embodiment of the invention, it is furthermore particularly preferable for a user to be able to undertake a modification of visualization parameters. Accordingly, a visualization module according to at least one embodiment of the invention preferably has a user interface for modifying visualization parameters by the user. By way of example, such visualization parameters are the viewing or illumination angle, the type of the color or contour display of the height conditions or the imaging preparation of the image data within the scope of imaging and, furthermore, the speed and/or frequency of dynamic changes, as well as the selection as to whether such changes are undertaken automatically by the visualization module or controlled by the user.

It is particularly preferable for selected bumps of the hollow organ to be marked by a user. The markings can then also be displayed in another—preferably three-dimensional—type of display. Such a marking is in general only effected virtually, and the display of the marking in other types of display means that the marking is transformed to these types of display together with the image data. For example, marking data obtained in this fashion in the virtual dissection can be transferred to displays such as the multi-planar reconstruction or a virtual flight and can be made available for subsequent users.

In principle, the image data can be obtained from all currently known imaging methods for hollow organs. When obtaining image data of a large intestine, these also include, for example, colonoscopy, i.e. endoscopy of the intestine by means of a rectally inserted probe. However, it is preferable for the image data to be segmented from the volume image data of a tissue region comprising the hollow organ, particularly preferably by using image data obtained by a tomographic system, in particular a computed tomography or magnetic resonance imaging system. On the one hand, this affords the possibility of a very detailed image display and on the other hand it affords the possibility of obtaining the image data non-invasively.

The method according to at least one embodiment of the invention affords the possibility of visualizing bumps in any type of hollow organ. In a particularly preferable fashion, however, the method is suitable for an intestine, preferably a large intestine, which is represented by the image data in its entirety or in sections. Precisely the large intestine is an organ with a complicated structure in terms of its shape and position, which, in addition, has a multiplicity of folds and other bumps. Detecting bumps which could indicate an illness is therefore very dependent on the experience of the medical personnel undertaking the findings. To this extent, at least one embodiment of the invention particularly displays all its stated advantages, when applied to the large intestine.

BRIEF DESCRIPTION OF THE DRAWINGS

In the following text, the invention will once again be explained in more detail on the basis of example embodiments and with reference to the attached figures. Here, the same components in the various figures are provided with identical reference numerals.

DETAILED DESCRIPTION OF THE EXAMPLE EMBODIMENTS

Figure 1:
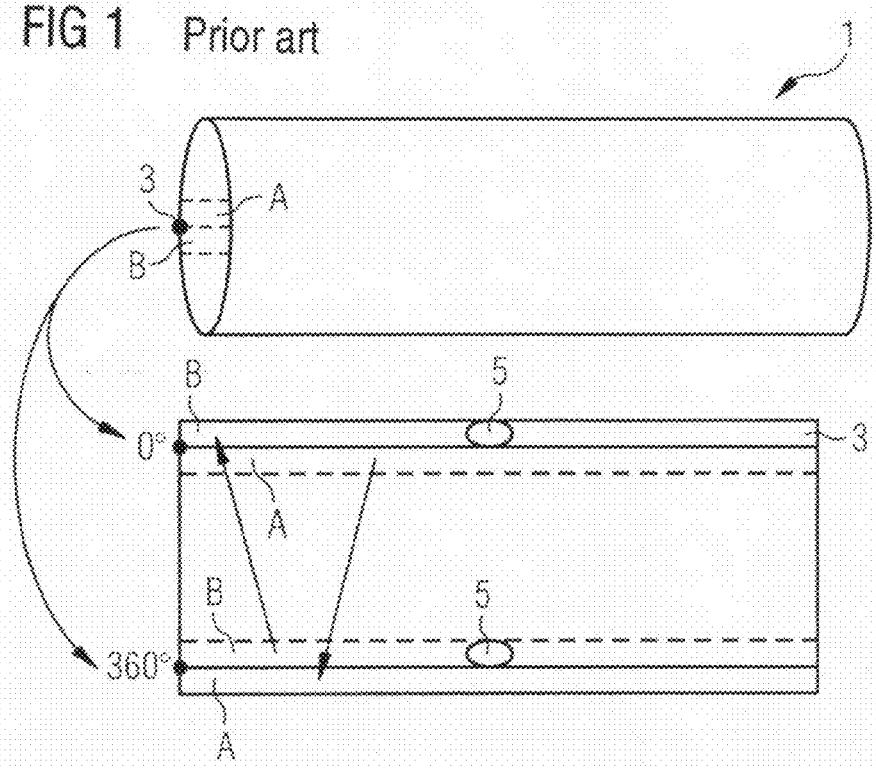
FIG. 1 shows an illustration of the principle of forming a virtual dissection of an arbitrary hollow organ in accordance with the prior art.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the figures, an intestine is in each case illustrated as an example of a hollow organ because the application of at least one embodiment of the invention for visualizing bumps of intestinal surfaces is an important field of application. However, this selection of the example does not limit embodiments of the invention to intestine-related applications.

FIG. 1 shows the functional schematic of the principle of the generation of a virtual dissection of a hollow organ 1 in accordance with the prior art. A hollow organ 1, formed in a simplified manner as a cylinder for reasons of clarity, is virtually cut open along a cutting edge 3 and rolled open. In the real image, an intestine is for example segmented from volume image data and the image data are virtually stretched in a direction of progression.

This virtual dissection can be seen in the lower illustration. It can be seen in this case that two overlap regions A, B are provided beyond the cutting edge 3 and can be seen twice in the illustration, respectively at the top and bottom. This correspondence is indicated by arrows. It is therefore not easy in this display to overlook a conspicuous bump 5, in this case a polyp, which lies exactly in the overlap region B. Instead, it is shown twice: once on the extreme edge at the top and once in a region above the extreme edge at the bottom of the illustration. The plane of the virtual dissection is exactly perpendicular to the viewing direction of a user.

Figure 2:
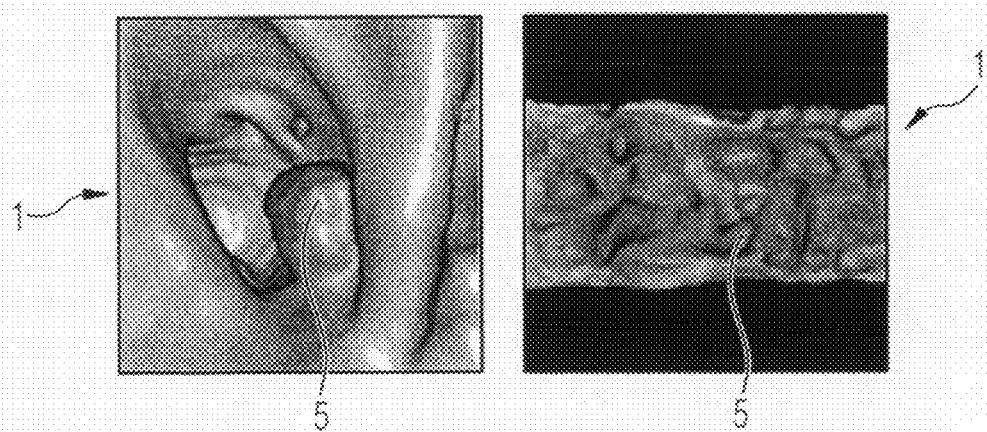
FIG. 2 shows a spatial display of a large intestine in the virtual flight and, parallel to this, a virtual dissection of the same region of the large intestine in accordance with the prior art.

FIG. 2 illustrates a virtual dissection on the basis of a concrete imaging display example. The left-hand side shows a screenshot of a virtual flight through a hollow organ, in this case a large intestine 1, which is based on image data generated by a slice image recording system. A polyp 5, that is to say a conspicuous bump, in this case protrudes into the large intestine 1. In the virtual dissection, shown on the right-hand side, this polyp 5 can only be dimly detected due to its small shadow in the plane. This is the starting point of an embodiment of the invention.

Figure 3:
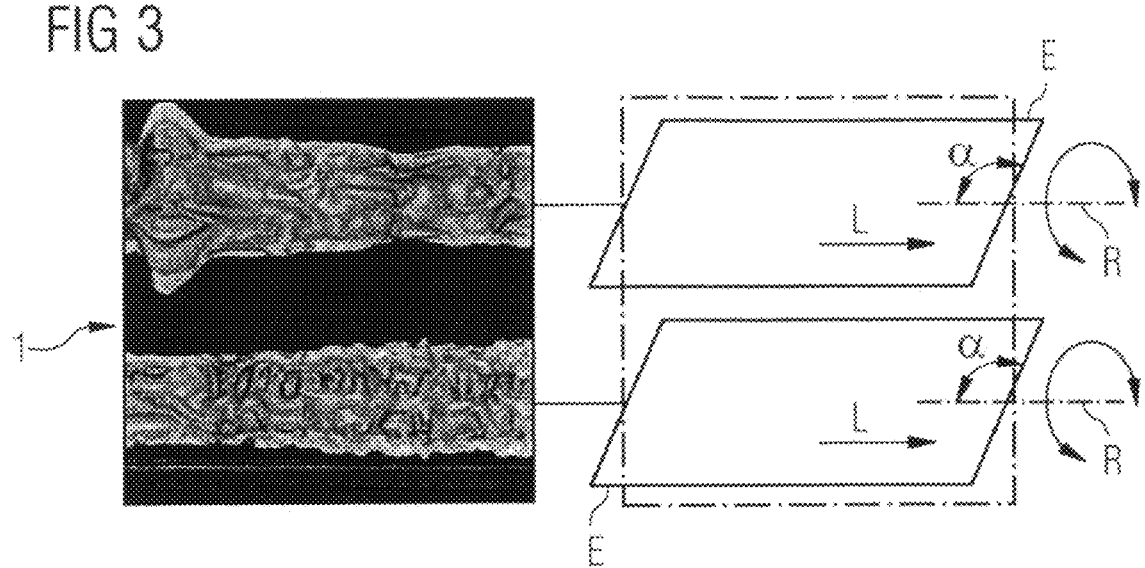
FIG. 3 shows a row-by-row display of two sections of a large intestine in the virtual dissection and an illustration of the principle of a first variant of the method according to an embodiment of the invention.

FIG. 3 shows two rows of an image display of a virtual dissection of a large intestine 1. For this purpose, the profile of the large intestine 1 was plotted from left to right and subdivided into individual sections, and the sections were placed one below the other in rows. Here, FIG. 3 only illustrates two selected rows. To the right of this, a principle is illustrated schematically as to how the bumps of the large intestine 1 can, according to a variant of the invention, be visualized in an improved fashion. To this end, the display plane E, lying perpendicular to the viewing direction, is firstly pivoted, that is to say about an axis of rotation R which in this case runs centrally in the illustration, parallel to the longitudinal direction L or to the direction of progression of the cutting edge 3 (not illustrated here—cf. FIG. 1). That is to say the viewing angle α of the observer to the display plane E changes.

By dynamic pivoting of this display plane E, either controlled by the user himself or carried out independently by a visualization module according to an embodiment of the invention, it becomes possible to develop a spatial sense despite the two-dimensional display and thus to see and detect bumps 5 (not illustrated here—cf. FIG. 1) from different perspectives as a result of this.

Figure 4:
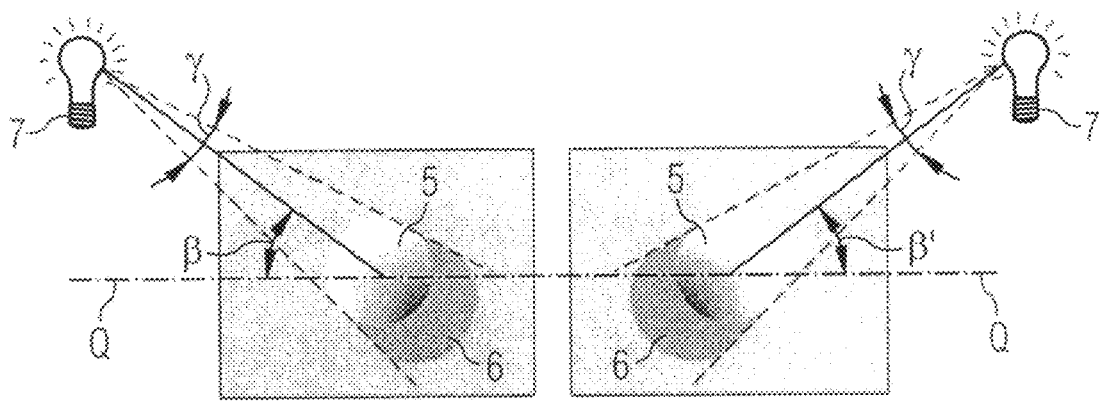
FIG. 4 shows a schematic illustration of the principle of a change in an illumination angle with respect to an object to be displayed.

A second possibility for displaying bumps 5 is shown in FIG. 4. A bump 5—illustrated in a simplified manner here as a hemispherical bulge—is illuminated by a virtual light source 7. The position of the light source 7 is changed such that it shines onto the bump 5 from two different angles of illumination (β, β') with respect to an axis Q of the image. Here, it is possible to not only vary the angle of illumination in the image plane, but also to pivot the virtual light source 7 out of the image plane, that is to say to vary the angle of elevation of the virtual light source 7 with respect to the image plane. The lamp aperture angle γ remains constant in the illustration of FIG. 4; however, it can alternatively or additionally also be varied. As a result of the hemispherical shape of the bump 5, a shadow 6 results which in each case lies on that side of the bump 5 which is precisely opposite the virtual light source 7. Depending on the type and shape of the bump 5, the shape of the shadow 6 can also vary, as a result of which it is in turn easier for an observer to be able to more precisely classify the character and peculiarities of different bumps.

Figure 5:
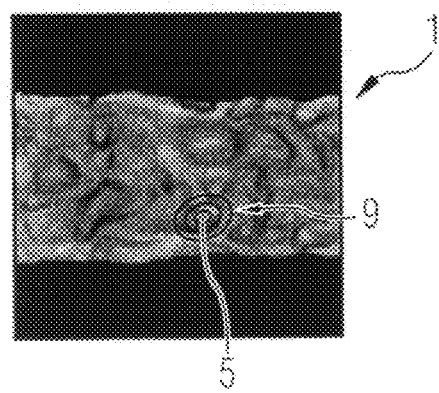
FIG. 5 shows a display of the principle of a third variant of an embodiment of the invention on the basis of a virtual dissection.

FIG. 5 illustrates the virtual dissection from FIG. 2, a conspicuous bump 5 now being made more recognizable by displaying height contours 9 which represent the height conditions of the surface of the large intestine 1 compared to the display plane E. In this manner, a topology becomes recognizable, similar to an image on a topographic map. Just as it is possible to recognize in such a map that a certain swathe of land is characterized by a hill and another by an elongate valley, it is also possible in this case to clearly distinguish between, for example, channel-like bumps running in the longitudinal direction, such as intestinal folds, and hemispherical bumps 5 such as polyps, as a result of which critical bumps can be discriminated by a user.

Figure 6:
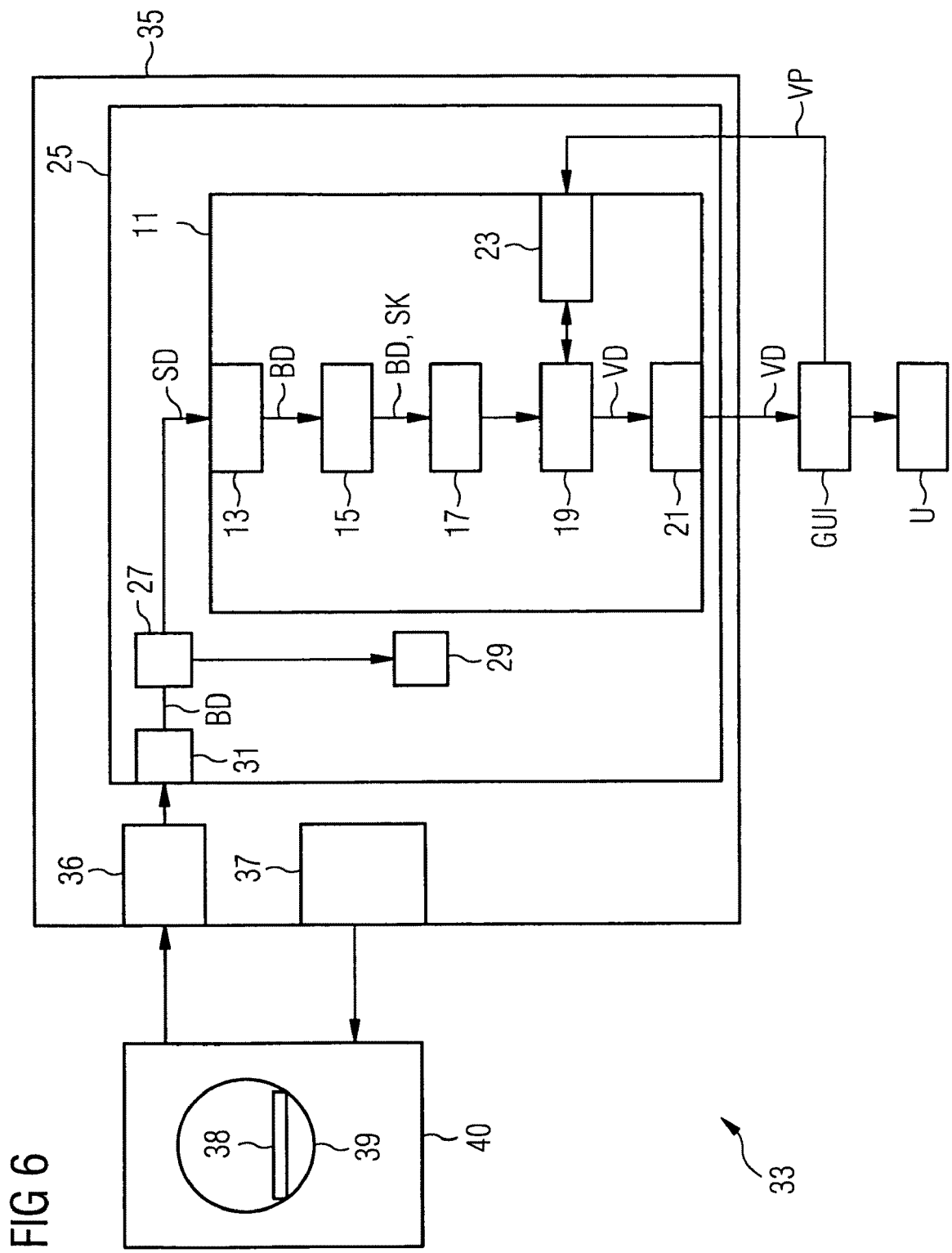
FIG. 6 shows a schematic block diagram of a tomographic system according to an embodiment of the invention with an image processing device according to an embodiment of the invention and a visualization module according to an embodiment of the invention.

FIG. 6 shows a schematic block diagram of a tomographic system 33 according to the invention. In addition to the actual scanner 40 with the patient tunnel 39 and the patient table 38, it comprises a control device 35 for actuating the scanner 40 with a multiplicity of very different hardware components 35 and software components. The components which are used to actuate the scanner 40 are illustrated here in a very schematic fashion as a control block 37.

Further components of the control device 35 are used to receive or acquire raw data and to reconstruct image data from the raw data. These components are illustrated schematically in the form of an image data acquisition block 36.

Furthermore, the tomographic system 33 can comprise a multiplicity of further conventional components which, however, do not have to be illustrated or explained here in any more detail because the principal methods of operation of tomographic systems, whether they be computed tomography scanners, magnetic resonance imaging scanners, PET/SPECT scanners, etc., are known to a person skilled in the art with reference to their basic operation and their design.

Moreover, in this case the control device 35 has an image processing device 25. The image processing device 25 in turn comprises an input interface 31, for transferring the image data BD from the image data acquisition block 36, and a plurality of image processing components 27, 29, as well as a visualization module 11 according to the invention. The latter has an input interface 13 and an output interface 21. Between these, a cutting edge definition unit 15, a preparation unit 17 and a visualization-support unit 19 are arranged as software modules on a processor. Furthermore, provision is made for a user interface 23 for modifying visualization parameters VP by a user U via a graphical user interface GUI. It is also possible to use the user interface to control further components of the control device 35, and hence the scanner 40 as well.

The following procedure is effected during the operation of the visualization module 11:

Image data BD from a hollow organ 1 is transferred from the image data acquisition block 36 to the image processing device 25 via the input interfaces 31. There it reaches a first image processing component 27 which in this case, as a segmentation module, ensures segmentation of the intestine in the image data BD and transmits the segmented image data SD to the input interface 13 of the visualization module 11. The original image data BD and/or the segmented image data SD can additionally be transferred to further image processing components, of which one image processing component 29 is illustrated as a block only on behalf of these. Using these additional image processing components, it is possible to effect the most varied different evaluations and/or preparations of the image data BD and/or the segmented image data SD.

From the input interface 13 of the visualization module 11, the segmented image data SD first of all reaches the cutting edge definition unit 15. There, a cutting edge 3 is drawn in the image data BD along the surface of the hollow organ 1 in the longitudinal direction L (cf. FIG. 1 to this end). The image data BD, together with the cutting edge data SK generated in the cutting edge definition unit 15 reach the preparation unit 17. There, the image data BD is used to display a virtual dissection of the hollow organ 1.

Visualization data VD is generated from the image data BD in the visualization-support unit 19. The visualization-support unit 19 is designed such that at least one of the following steps can be carried out with its help: 100641 Changing the viewing angle α while the hollow organ 1 is displayed; changing the illumination angle, that is to say the angle of illumination β, β' and/or the lamp aperture angle γ, while the hollow organ 1 is displayed; plotting a color and/or contour display 9 of the height conditions of the surface with respect to the display plane E. The visualization data VD generated in this fashion is transmitted to the user interface GUI, and hence to a user U, via the output interface 21. The image data BD is visualized for the user U as described above such that said user can simply and effectively detect bumps 3 on the surface of the hollow organ 1.

In conclusion, reference is once again made to the fact that the method described above in great detail and the illustrated visualization module are only example embodiments which can be modified by a person skilled in the art in very different ways without leaving the scope of the invention.

In particular, the image processing device need not be integrated in the control device of a tomographic system; rather, it can be incorporated as self-contained unit, for example as a findings station in a network, in particular in a radiological information system (RIS), and it can accept the image data from different tomography scanners via the network or in any other manner. Furthermore, it is also possible for additional components to be connected to the image processing device, such as, for example, printers, or the image processing device or the visualization module can be constructed from a number of spatially separated components which are, however, suitably connected in terms of signal processing technology or data processing technology.

Furthermore, use of the indefinite article "a" or "an" does not preclude the possibility of the relevant features being present a number of times.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method, comprising:
   acquiring recorded image data of a hollow organ using an imaging system;
   drawing a cutting edge in the acquired image data along a surface of the hollow organ in the longitudinal direction;
   preparing the acquired image data to display the surface of the hollow organ along a plane on which the surface is plotted in an opened-up fashion; and
   changing at least a viewing angle during a display of the hollow organ, the changing the viewing angle including rotating the plane dynamically along an axis running parallel to the cutting edge, to change the viewing angle during a dynamic variation of the display of the hollow organ.

2. The method as claimed in claim 1, further comprising changing a position of a virtual light source.

3. The method as claimed in claim 2, wherein a plurality of virtual light sources are used.

4. The method as claimed in claim 3, further comprising switching virtual light sources on or off.

5. The method as claimed in claim 1, further comprising using a plurality of virtual light sources.

6. The method as claimed in claim 5, further comprising switching virtual light sources on or off.

7. The method as claimed in claim 1, further comprising receiving notification of modification of visualization parameters by a user.

8. The method as claimed in claim 7, wherein the method is for visualizing bumps of an inner surface of a hollow organ, selected bumps of the hollow organ being marked by the user, and wherein markings by the user are also displayed in a different type of display.

9. The method as claimed in claim 8, wherein the markings are displayed in a three-dimensional display.

10. The method as claimed in claim 1, wherein the image data is segmented from volume image data of a tissue region comprising the hollow organ.

11. The method as claimed in claim 10, wherein the volume image data is obtained with the aid of a tomographic system.

12. The method as claimed in claim 1, wherein the image data represents an intestine, either in its entirety or in sections thereof.

13. The method as claimed in claim 12, wherein the intestine is a large intestine.

14. The method of claim 1, wherein the changing the viewing angle includes changing an illumination angle during a display of the hollow organ.

15. A visualization module, comprising:
an input interface to obtain image data of a hollow organ from an imaging system;
a cutting edge definition unit to draw a cutting edge in the obtained image data along a surface of the hollow organ in a longitudinal direction;
a preparation unit to prepare the image data to display the surface of the hollow organ along a plane on which the surface is plotted in an opened-up fashion;
a visualization-support unit to generate visualization data from the image data and to, during operation, change at least a viewing angle while the hollow organ is displayed, the viewing angle change being carried out by a dynamic rotation of the plane along an axis running parallel to the cutting edge; and
an output interface for the visualization data.

16. The visualization module as claimed in claim 15, further comprising a user interface for modifying visualization parameters by a user.

17. An image processing device comprising the visualization module as claimed in claim 16.

18. A tomographic system comprising the image processing device as claimed in claim 17.

19. An image processing device comprising the visualization module as claimed in claim 15.

20. A tomographic system comprising the image processing device as claimed in claim 19.

21. The visualization module as claimed in claim 15, wherein the visualization module is for visualizing bumps of an inner surface of the hollow organ.

22. The visualization module of claim 15, wherein the visualization-support unit is further configured to change an illumination angle while the hollow organ is displayed.

23. A non-transitory computer readable medium including program segments for, when executed on a processor of a programmable image processing system, causing the image processing system to
acquire recorded image data of a hollow organ;
draw a cutting edge in the acquired image data along a surface of the hollow organ in the longitudinal direction;
prepare the acquired image data to display the surface of the hollow organ along a plane on which the surface is plotted in an opened-up fashion; and
change at least a viewing angle during a display of the hollow organ, the changing the viewing angle including rotating the plane dynamically along an axis running parallel to the cutting edge to change the viewing angle during a dynamic variation of the display of the hollow organ.

* * * * *